United States Patent
Brown

(10) Patent No.: US 9,545,427 B2
(45) Date of Patent: *Jan. 17, 2017

(54) THERAPEUTIC USES OF ALLOGENEIC MYELOID PROGENITOR CELLS

(71) Applicant: THE BOARD OF TRUSTEES OF THE LELAND STANFORD JUNIOR UNIVERSITY, Palo Alto, CA (US)

(72) Inventor: Janice Marie Brown, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 133 days.

This patent is subject to a terminal disclaimer.

(21) Appl. No.: 14/642,254

(22) Filed: Mar. 9, 2015

(65) Prior Publication Data

US 2015/0174167 A1  Jun. 25, 2015

Related U.S. Application Data

(60) Continuation of application No. 12/875,022, filed on Sep. 2, 2010, now Pat. No. 8,980,329, which is a division of application No. 11/270,710, filed on Nov. 8, 2005, now Pat. No. 7,811,815.

(60) Provisional application No. 60/628,388, filed on Nov. 15, 2004.

(51) Int. Cl.
| | |
|---|---|
| *A61K 35/26* | (2015.01) |
| *C12N 5/00* | (2006.01) |
| *C12N 5/02* | (2006.01) |
| *A61K 35/15* | (2015.01) |
| *A61K 38/18* | (2006.01) |
| *A61K 38/19* | (2006.01) |
| *A61K 35/19* | (2015.01) |

(52) U.S. Cl.
CPC .............. *A61K 35/15* (2013.01); *A61K 35/19* (2013.01); *A61K 38/1816* (2013.01); *A61K 38/193* (2013.01); *A61K 38/196* (2013.01)

(58) Field of Classification Search
None
See application file for complete search history.

(56) References Cited

U.S. PATENT DOCUMENTS

| 6,465,247 | B1 | 10/2002 | Weissman et al. |
| 6,761,883 | B2 | 7/2004 | Weissman et al. |
| 7,300,760 | B2 | 11/2007 | Weissman et al. |
| 2002/0086422 | A1 | 7/2002 | Weissman et al. |
| 2003/0060425 | A1 | 3/2003 | Ahlem et al. |
| 2005/0215473 | A1 | 9/2005 | Alvarez et al. |

OTHER PUBLICATIONS

American Red Cross, Practice Guidelines for Blood Transfusion. A Compilation from Recent Peer-Reviewed Literature, 2nd Edition, 2007 [retrieved on Oct. 28, 2009]. Retrieved from the internet: http://www.redcross.org./www-files/documents/workingwiththeredcross/practiceguidelinesforbloodtrans.pdf>, pp. 1-64.
Arbor et al., Common lymphoid progenitors from MHC-mismatched donors engraft without inducing GVHD, Blood, 2003, 102: 3504.
Bitmansour et al., Myeloid progenitors protect against invasive aspergillosis and Pseudomonas aeruginosa infection following hematopoietic stem cell transplantation, Blood, 2002, 100(13): 4660-7.
Booth et al., Protection against mucosal injury by growth factors and cytokines, J Natl Cancer Inst Monogr, 2001, 29:16-20.
Cairo et al., Circulating granulocyte colony-stimulating factor (G-CSF) levels after allogeneic and autologous bone marrow transplantation: endogenous G-CSF production correlates with myeloid engraftment, Blood, 1992, 79:1869-73.
Fugier-Vivier; et al., "Plasmacytoid precursor dendritic cells facilitate allogeneic hematopoietic stem cell engraftment", The Journal of Experimental Medicine (Feb. 2005), 201(3):373-383.
Harman; et al., "Mouse plasmacytoid dendritic cells derive exclusively from estrogen-resistant myeloid progenitors", Blood (Aug. 2006), 108(3):878-885.
Oksanen et al., Impact of leucocyte-depleted blood components on the haematological recovery and prognosis of patients with acute myeloid leukaemia. Finnish Leukemia Group, Br J Haematol, 1993, 84:639-47.
Petersdorf et al., High resolution donor HLA-matching: Saving Lives, Center for international Blood and Marrow Transplant Research, 2006, 12:1-22.
Rieger et al., Infectious complications after allogeneic stem cell transplantation: incidence in matched-related and matched-unrelated transplant settings, Transpl Infect Dis, 2009, 11:220-6.
Sasazuki et al., Effect of matching of class I HLA alleles on clinical outcome after transplantation of hematopoietic stem cells from an unrelated donor. Japan Marrow Donor Program, N Engl J Med, 1998, 339:1177-85.

(Continued)

Primary Examiner — Michail Belyavskyi
(74) Attorney, Agent, or Firm — Pamela J. Sherwood; Bozicevic, Field & Francis LLP

(57) ABSTRACT

Myeloid function is enhanced by transplantation or infusion of allogeneic myeloid progenitor cells, including CMP, GMP, MEP and MKP cell subsets. Myeloid progenitors ameliorate sequelae of anemia and thrombocytopenia, and can prevent or treat gastrointestinal mucositis associated with chemotherapy, radiotherapy, and the like. The transplantation or infusion may be performed in the absence of HLA typing, and the cells may be mismatched at one or more Class I HLA loci. The transplantation may provide for treatment of ongoing disease, or prevention of disease in high risk patients.

28 Claims, 7 Drawing Sheets

(56) References Cited

OTHER PUBLICATIONS

Theilgaard-Monch et al., Single leukapheresis products collected from healthy donors after the administration of granulocyte colony-stimulating factor contain ten-fold higher numbers of long-term reconstituting hematopoietic progenitor cells than conventional bone marrow allografts, Bone Marrow Trnasplant, 1999, 23:243-9.

Wardley et al., Prospective evaluation of oral mucositis in patients receiving myeloablative conditioning regimens and haemopoietic progenitor rescue, Br J Haematol, 2000, 110:292-9.

Wintrhop university Hospital, Institute for Family Care, Comlete Blood Count (CBC), 2008 [retrieved on Oct. 28, 2009]. Retrieved from the Internet: http://www.winthrop.org/CCK/Understand-Childhood-Cancers-Blood-Disorders.cfm?page=cb>, pp. 1-6.

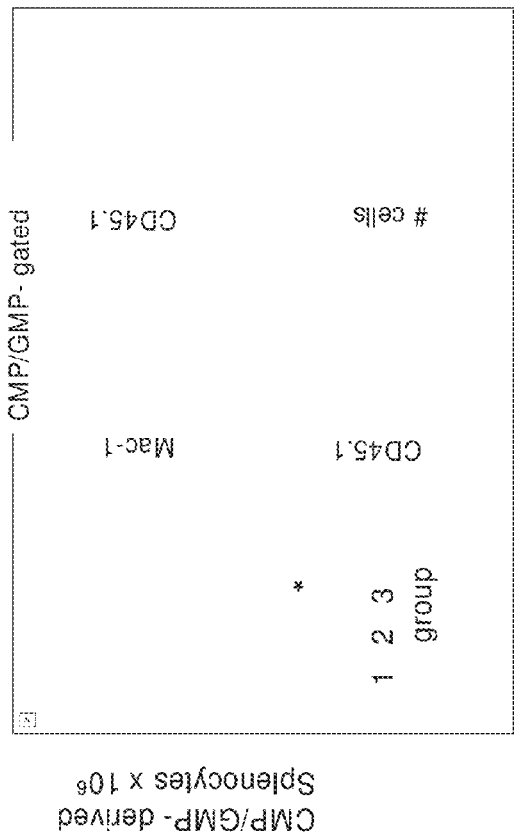
FIG. 1A Chimerism analysis: Spleen
| Splenocytes (x10e5) | (1) Congenic | | (2) Matched unrelated | | (3) MHC-mismatched | |
|---|---|---|---|---|---|---|
| | mean | sd | mean | sd | mean | sd |
| Total CMP/GMP-derived | 43.9 | 14.0 | 21.8 | 13.1 | 1.4 * | 1.7 |
| Total Granulocytes | 26.6 | 9.3 | 10.5 | 6.5 | 0.8 * | 1.1 |
| CMP/GMP-derived Granulocytes | 26.6 | 9.3 | 10.5 | 6.5 | 0.8 * | 1.1 |
■ granulocytes
* $P=0.02$, all others $P=NS$

FIG. 1B Chimerism analysis: Bone Marrow
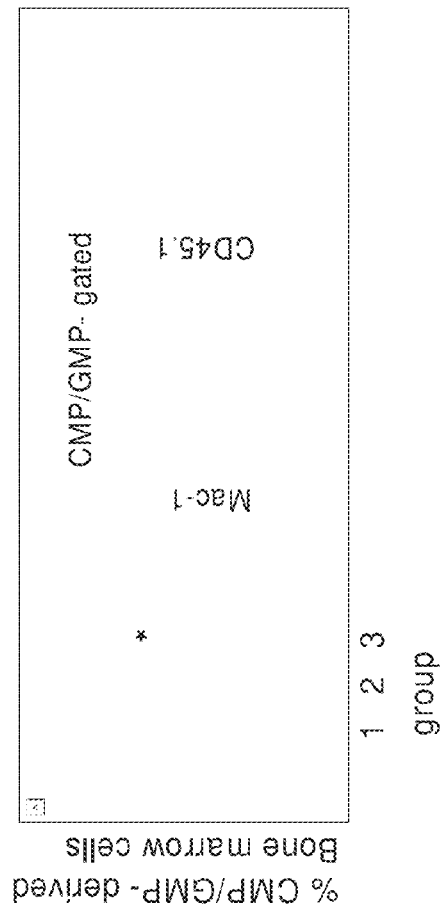
| Bone Marrow | (1) Congenic | | (2) Matched unrelated | | (3) MHC- mismatched | |
|---|---|---|---|---|---|---|
| | mean | sd | mean | sd | mean | sd |
| CMP/GMP- derived (%) | 42.9 | 16.8 | 35.3 | 16.1 | 20.1* | 10.8 |
| Granulocytes (%) | 50.4 | 13.5 | 59 | 11.7 | 71.8 | 5.8 |
| CMP/GMP- derived Granulocytes (%) | 77.4 | 8.8 | 81.3 | 5.1 | 83.6 | 5.1 |

FIG. 1C     Experimental Design: ENGRAFTMENT

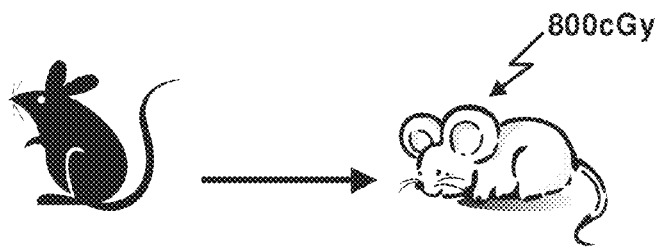

10⁴ CMP and 2x10⁴ GMP
CMP: Lin⁻Sca-1⁻c-Kit⁺CD34⁺FcγR$^{lo}$
GMP: Lin⁻Sca-1⁻c-Kit⁺CD34⁺FcγR$^{hi}$

| CMP/GMP Donor | Recipient | Antigen disparity |
|---|---|---|
| C57/BL6-Ly5.2 | C57/BL6 | congenic |
| C57/BL6-Ly5.2 | BALB.B | Matched unrelated |
| C57/BL6-Ly5.2 | Balb/c | MHC-mismatched |

Analysis day 7 post-transplantation:
Absolute counts and phenotype by FACS
of Blood, spleen and bone marrow Table 1. Complete Blood Counts day 7 post-transplantation

| Cell Type | units | Congenic | | Matched unrelated | | MHC-mismatched | |
|---|---|---|---|---|---|---|---|
| | | mean | sd | mean | sd | mean | sd |
| RBC | x10e6/uL | 7 | 3 | 9 | 0 | 8 | 1 |
| Hematocrit | % | 31 | 12 | 40 | 2 | 39 | 3 |
| WBC | /uL | 200 | 310 | 91 | 79 | 78 | 88 |
| ANC | /uL | 125 | 183 | 60 | 47 | 38 | 34 |

*P*=NS for all groups

Experimental Design: PROTECTION AGAINST ASPERGILLUS

| CMP/GMP Donor | HSC Donor | Recipient |
|---|---|---|
| C57/BL6-Ly5.2 (H2b) | C57/BLKa.Thy1.1 (H2b) | BALB.B (H2b) |
| C57/BL6-Ly5.2 (H2b) | B10.D2.Thy1.1 (H2d) | Balb/c (H2d) |

Matched unrelated CMP/GMP

- ● HSC + $10^4$ CMP + $2 \times 10^4$ GMP (n=10)
- ○ HSC (n=10)
  * $P=0.02$

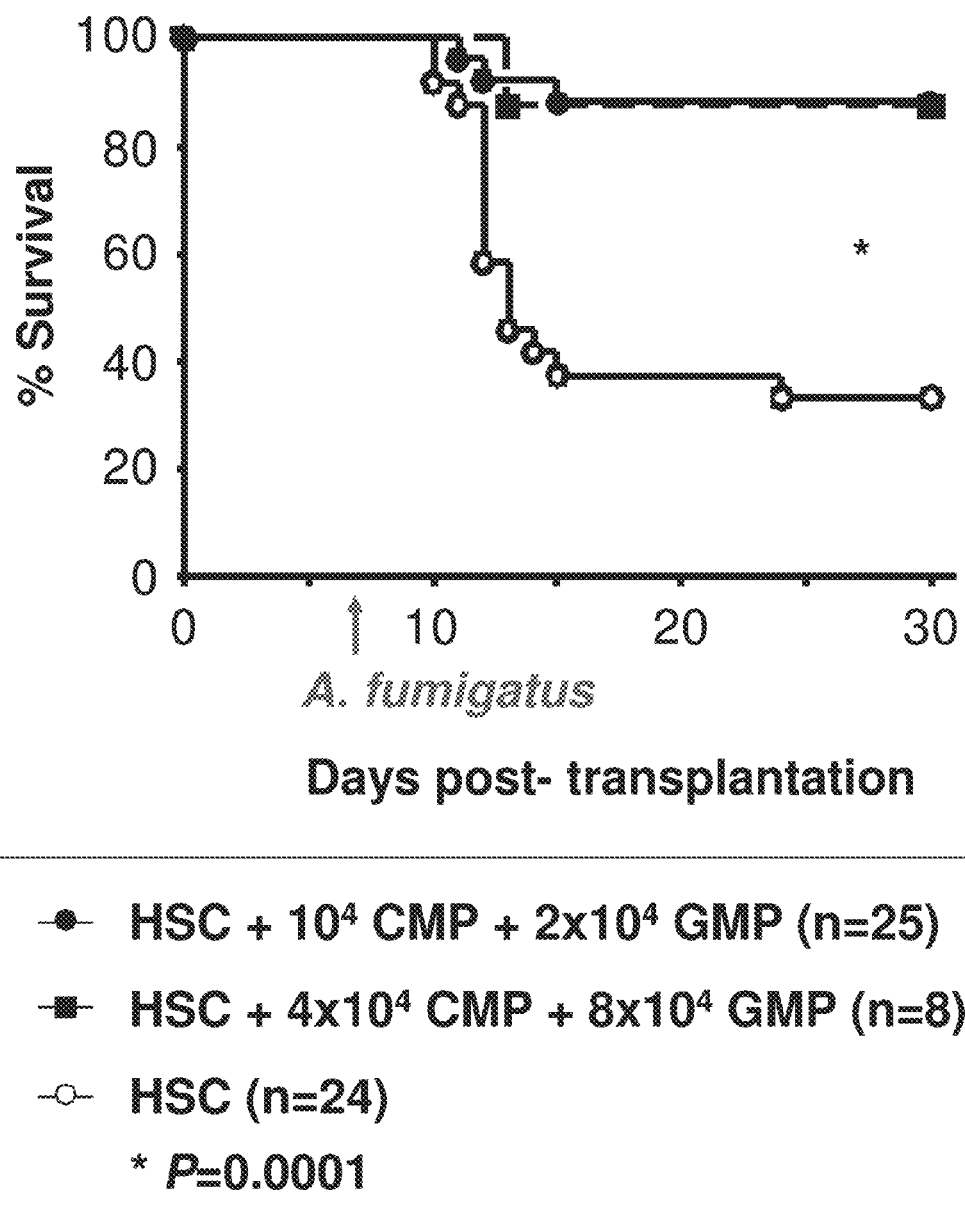

THERAPEUTIC USES OF ALLOGENEIC MYELOID PROGENITOR CELLS

CROSS REFERENCE

This application claims benefit and is a Continuation of application Ser. No. 12/875,022 filed Sep. 2, 2010, which is now U.S. Pat. No. 8,980,329 issued Mar. 17, 2015, which is a Divisional and claims the benefit of application Ser. No. 11/270,710, filed Nov. 8, 2005, which is now U.S. Pat. No. 7,811,815 issued Oct. 12, 2010, which claims benefit of U.S. Provisional Patent Application No. 60/628,388, filed Nov. 15, 2004, which patents and applications are incorporated herein by reference in their entirety.

BACKGROUND OF THE INVENTION

Blood cells are derived from hematopoietic stem and progenitor cells in the bone marrow. During the process of differentiation, a pluripotential stem cell gives rise to progenitor and effector cells that have a more limited developmental repertoire, and which may give rise only to cells within a particular lineage. The common myeloid progenitor cell is the precursor of megakaryocytes, erythrocytes, granulocytes, macrophages, dendritic cells, and mast cells. These cells comprise the innate immune system, which is involved in antigen presentation, phagocytosis, and other non-antigen specific responses.

Macrophages are one of the three types of phagocytic cells in the immune system. They are the mature form of monocytes, which circulate in the blood and differentiate continuously into macrophages upon migration into the tissues. Dendritic cells are also phagocytic, and are specialized to take up antigen and display it for recognition by lymphocytes. Mast cells also differentiate in the tissues. They mainly reside near small blood vessels and, when activated, release substances that affect vascular permeability. Although best known for their role in orchestrating allergic responses, they are believed to play a part in protecting mucosal surfaces against pathogens.

There are three types of granulocyte, all of which are relatively short lived and are produced in increased numbers during immune responses, when they leave the blood to migrate to sites of infection or inflammation. Neutrophils, which are the third phagocytic cell of the immune system, are the most numerous and most important cellular component of the innate immune response: hereditary deficiencies in neutrophil function lead to overwhelming bacterial infection, which is fatal if untreated. Eosinophils are thought to be important chiefly in defense against parasitic infections, because their numbers increase during a parasitic infection. The function of basophils is probably similar and complementary to that of eosinophils and mast cells.

Patients suffering from various diseases and therapies may have a deficiency on one or more of these myeloid lineage cells, which deficiency can result in increased susceptibility to bacterial and fungal infections. Leukopenia is usually characterized by a reduced number of blood neutrophils, although a reduced number of lymphocytes, monocytes, eosinophils, or basophils may also contribute to the decreased total cell count. Neutropenia accompanied by monocytopenia and lymphocytopenia is often a more serious disorder than neutropenia alone. Thrombocytopenia can also be a problem for myelosuppressed patients, stemming from failed megakaryocyte production. Severe thrombocytopenia results in a typical pattern of bleeding. Platelet transfusions can be used, but with discretion, because they may lose their effectiveness with repeated use owing to the development of platelet alloantibodies.

For example, patients undergoing hematopoietic cell transplantation (HCT) receive myeloablative doses of chemo-radiation therapy that lead to depletion of hematopoietic stem cells (HSC), progenitor cells and mature cells, thus leading to a phase of treatment related pancytopenia. The reconstitution of a functional immune system after HCT is dependent upon the de novo regeneration of all hematopoietic lineages from HSC and progenitor cells and on the function of mature cells contained in the graft. Infections after HCT typically follow a reproducible time pattern correlating with the kinetics of immune reconstitution, and despite aggressive treatment, the mortality rate of infections in the absence of immune reconstitution can be very high.

Drugs are one of the most common causes of neutropenia. Drug-induced neutropenia has several underlying mechanisms (immune, toxic, idiosyncratic, or hypersensitivity reactions), including severe neutropenia that predictably occurs after large doses of cytoreductive cancer drugs or radiotherapy and from that caused by viral infections. Cytotoxic chemotherapy induces neutropenia because of the high proliferative rate of neutrophil precursors and the rapid turnover of blood neutrophils. Impaired neutrophil production can also occur when leukemia, myeloma, lymphoma, or metastatic solid tumors infiltrate and replace the bone marrow. Tumor-induced myelofibrosis may further extenuate neutropenia. Myelofibrosis can also occur from granulomatous infections, Gaucher's disease, and radiotherapy.

Patients whose neutropenia is secondary to acquired disorders of production arising from cancer or from chemotherapy are more likely to develop serious bacterial or fungal infections because their overall immune system is compromised. The integrity of the skin and mucous membranes, the vascular supply to tissue, and the nutritional status of the patient also influence the risk of infections in acute neutropenia. Patients may also suffer from genetic or primary deficiencies of myeloid cells and are highly susceptible to infection as is seen, for example, in children with chronic granulomatous disease.

The treatment and prevention of infections, particularly in patients suffering or at risk of myeloid cell deficiencies, are of great medical concern. The present invention addresses these issues.

RELEVANT LITERATURE

U.S. Pat. Nos. 6,465,247 and 6,761,883, herein specifically incorporated by reference, characterize mammalian myeloid progenitor cells. Bitmansour et al (2002) Blood 100(13):4660-7 cotransplant congenic common myeloid progenitors (CMP) and granulocyte-monocyte progenitors (GMP) with a graft containing hematopoietic stem cells to enhance reconstitution of a tissue myeloid pool for protection against lethal challenge with fungal and bacterial pathogens. Arber et al. (2003) Blood 102:3504 provides an abstract relating to engraftment and protection with MHC-mismatched committed myeloid progenitors.

SUMMARY OF THE INVENTION

Compositions and methods are provided for enhancement of myeloid function in an individual, through transplantation or infusion of allogeneic or xenogeneic myeloid progenitor cells. The transplantation or infusion of these progenitor cells provides for treatment of ongoing disease or infection, or prevention of disease or infection, e.g. in high risk patients. It is also shown that transplantation or infusion of these progenitor cells provides for the treatment or prevention of radiation-injured mucosa, e.g. in gastrointestinal mucositis, and the like, which can be the result of chemotherapy, radiation therapy, and the like.

Individuals that benefit from the methods of the invention include immunocompromised patients having a deficiency in myeloid or erythroid cell function, e.g. following myeloablative doses of chemotherapy or radiation therapy; patients suffering from neutropenia; patients suffering from thrombocytopenia; patients suffering from chronic disorders such as chronic granulomatous disease; sickle cell disease; and the like.

The myeloid progenitor cells comprise one or more of: common myeloid progenitor cells (CMP); and the committed myeloid progenitors: erythroid/megakaryocytic progenitor (MEP), granulocyte/monocyte progenitors (GMP); and megakaryocyte progenitor (MKP). Generally the myeloid progenitors are initially purified, and may be provided to the patient in a purified form, or reconstituted as a mixture of cells, e.g. combined with mature platelets, red blood cells, stem cells, etc. The cells are administered to the individual in a biologically effective dose, e.g. by intravenous injection, etc. The myeloid progenitor cells will usually have one or more Class I HLA mismatches relative to the recipient, and administration may be performed without HLA testing of the recipient, although in certain embodiments of the invention the myeloid progenitor cells may be HLA matched.

The cell therapy of the invention may be combined with administration of cells, including hematopoietic stem cells; and may be combined with administration of cytokines, particularly cytokines that stimulate growth or enhance function of myeloid or erythroid lineage cells, e.g. G-CSF; GM-CSF; thrombopoietin; erythropoietin; and the like. The cell therapy may also be combined with agents including antifungal agents; antibiotics; anti-parasitic agents; and the like, as appropriate. In some embodiments of the invention, the myeloid progenitor cells of the invention are co-formulated with such cytokines and/or agents.

BRIEF DESCRIPTION OF THE DRAWINGS

FIGS. 1A-1C. Engraftment of CMP/GMP with different donor-host antigen disparities. Absolute counts of CMP/GMP-derived splenocytes (A) or percentages of CMP/GMP-derived bone marrow cells on day 7 post-transplantation after transplantation of $10^4$ CMP and $2\times10^4$ GMP in congenic, MHC-matched or MHC-mismatched hosts. Granulocytes (Mac-$1^+$Gr-$1^+$ cells) are shown in black. CMP/CMP gave rise to cells of the myelomonocytic, erythroid and dendritic cell lineages as shown in spleen or bone marrow (B) with a similar distribution in the three donor-host mouse strain combinations tested. CMP/GMP-engraftment was significantly less in MHC-mismatched hosts as compared to congenic or MHC-matched hosts. Group 1 vs group 3 *P=0.012, group 2 vs group 3 **P=0.02. Design of Experiment shown in FIG. 1C.

FIG. 2A-2B. Protection against *Aspergillus fumigatus* infection. (A) MHC-matched model (Table 1 group 4). HSC were harvested from C57BL/Ka-Thy1.1 ($H2^b$) and CMP/GMP from C57BL/6-Ly5.2 ($H2^b$) mice. Mice were transplanted with 500 HSC alone (○, n=10, 40% survival) or 500 HSC and $10^4$ CMP and $2\times10^4$ GMP (●, n=10, 90% survival). *P=0.02 (● versus ○). (B) MHC-mismatched model (Table 1 group 5) HSC are from B10.D2.Thy1.1 ($H2^d$) and CMP/GMP from C57BL/6-Ly5.2 ($H2^b$). Mice were transplanted with 500 HSC alone (○, n=24, 33% survival) or with 500 HSC and $10^4$ CMP and $2\times10^4$ GMP (●, n=25, 88% survival) or with 500 HSC and $4\times10^4$ CMP and $8\times10^4$ GMP (■, n=8, 88% survival). *P<0.0001 (● versus ○) and **P=0.01 (■ versus ○). P=0.99 (● versus ■).

DESCRIPTION OF THE SPECIFIC EMBODIMENTS

Figure 1C:
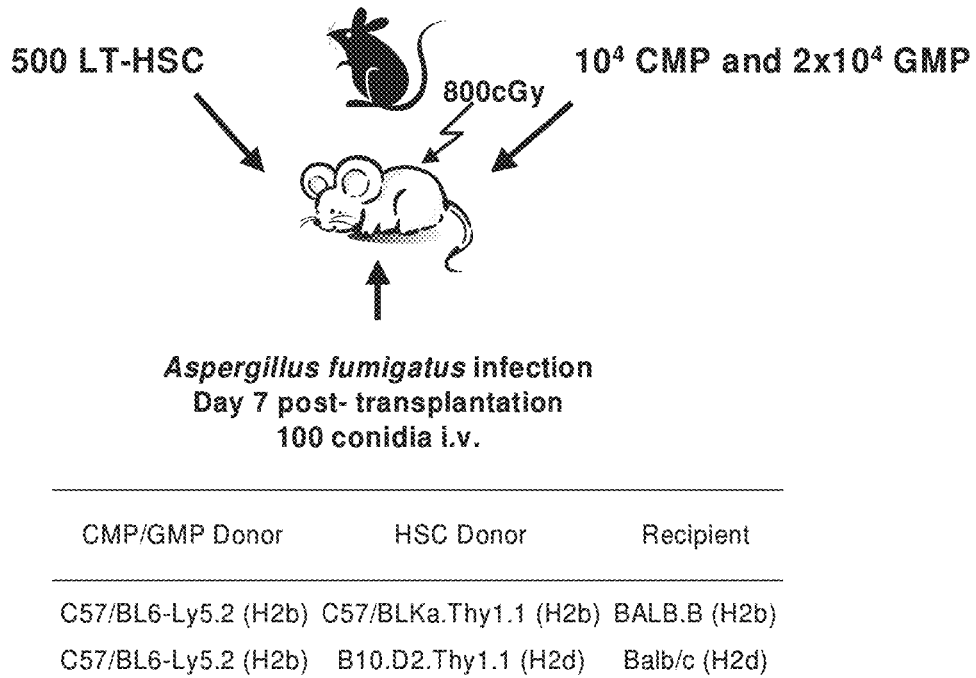

Myeloid function is enhanced in an individual through transplantation of allogeneic or xenogeneic myeloid progenitor cells, where the cells comprise one or more of: common myeloid progenitor cells (CMP); and committed myeloid progenitors: erythroid/megakaryocytic progenitor (MEP), granulocyte/monocyte progenitors (GMP); and megakaryocyte progenitor (MKP). The myeloid progenitor cells may have one or more Class I HLA mismatches relative to the recipient, and administration is optionally performed without HLA testing of the recipient. The myeloid progenitor cells may be obtained from bone marrow, mobilized peripheral blood, etc., and may be used fresh, frozen, after in vitro expansion, and the like. The myeloid progenitor cells may be administered in combination with committed cells in the lineage, which committed cells can be immature cells, platelets, etc.

The methods of the invention find use in the prevention and treatment of infection, particularly infections that are at least partially controlled by the innate immune system, which system includes dendritic cells, monocytes, macrophages, neutrophils, etc., and which pathogens may include viruses, such as CMV; fungal pathogens such as *Aspergillus* species; bacteria such as *Salmonella*; and protozoan pathogens, such as *Toxoplasma*. The methods of the invention also find use in alleviating gastrointestinal mucositis, which is a serious complication of immunosuppression, for example resulting from chemotherapy, radiotherapy, and the like.

In some embodiments of the invention, infection is a fungal infection. Mycoses may be caused by primary pathogenic and opportunistic fungal pathogens. The primary pathogenic fungi are able to establish infection in a normal host; whereas, opportunistic pathogens require a compromised host in order to establish infection (e.g., cancer, organ transplantation, surgery, and AIDS). Primary systemic fungal pathogens include *Coccidioides immitis, Histoplasma capsulatum, Blastomyces dermatitidis*, and *Paracoccidioides brasiliensis*. Opportunistic fungal pathogens include

*Cryptococcus neoformans, Candida* spp., *Aspergillus* spp., *Penicillium marneffei*, the *Zygomycetes, Trichosporon beigelii*, and *Fusarium* spp.

Myeloid Progenitors.

As used herein, the term refers generally to a class of mammalian cells that differentiate into cells of a myeloid lineage, and which lack the potential to differentiate into lymphoid lineages, which class includes CMP, GMP, MEP and MKP cells, as defined below. These cells provide for physiological functionality, such as protection from fungal infection, production of platelets and erythrocytes, etc., even in the presence of one or more MHC Class I antigen differences between donor and host. Following transplantation, the presence of the donor cells and progeny thereof is transient, where substantially all of the detectable donor cells are gone at about 4 weeks post-transplantation. These progenitors are capable of rapid differentiation activity in vivo. CMP cells give rise to Gr-1+/Mac-1+ myelomonocytic cells and megakaryocytic colonies, as well as TER119+ erythroid cells in spleen and bone marrow. The GMP progenitor population gives rise to Gr-1+/Mac-1+ cells; and the MEP progenitor population to megakaryocytes and erythroid cells.

The myeloid progenitor subsets are isolated from any source of hematopoietic progenitor cells, which may be fetal, neonatal, juvenile or adult, including bone marrow, spleen, liver, umbilical cord blood, peripheral blood, mobilized peripheral blood, yolk sac, etc. For peripheral blood, progenitor cells are mobilized from the marrow compartment into the peripheral bloodstream after treatment with chemotherapy; G-CSF or GM-CSF, or both. A number of single and combination chemotherapeutic agents have been used to mobilize PBPCs. In administering these agents, a balance must be found in all cases between effective PBPC mobilization and possible damage to the hematopoietic stem cell pool and overall patient tolerance. Paclitaxel has been found to effectively mobilize PBPCs without damaging the stem cell pool. A review of peripheral blood stem cells may be found in Shpall et al. (1997) *Annu Rev Med* 48:241-251, and the characterization of stem cell mobilization in Moog et al. (1998) *Ann Hematol* 77(4):143-7. As an alternative source of cells, progenitor cells may be derived from the in vitro culture of stem cells, e.g. embryonic stem cells, embryonic germ cells, hematopoietic stem cells, etc.

The progenitor cells may be obtained from any mammalian species, e.g. equine, bovine, porcine, canine, feline, rodent, e.g. mice, rats, hamster, primate, etc., particularly human. The tissue may be obtained by biopsy or aphoresis from a live donor, or obtained from a dead or dying donor within about 48 hours of death, or freshly frozen tissue, tissue frozen within about 12 hours of death and maintained at below about −20° C., usually at about liquid nitrogen temperature (−180° C.) indefinitely.

For most purposes, the myeloid progenitor cells are isolated from other hematopoietic cells, even when a defined cocktail of cells is ultimately provided to a patient. The isolated population will usually have at least about 75% cells of the selected phenotype, more usually at least 85% cells of the selected phenotype; and may have 95% cells of the selected phenotype. For some purposes, the selected cells will comprise a single myeloid progenitor, e.g. CMP. For other purposes, the selected cells will comprise two or more myeloid progenitors, e.g. CMP and GMP; CMP and MEP; CMP, MEP and MKP; CMP, GMP and MEP; and the like.

For selection of CMP in combination with GMP and MEP, the cells may be selected for the phenotype Thy-1$^-$, IL-7R$\alpha^-$, Lin$^-$, and CD38$^+$. For selection of CMP in combination with GMP, the cells may further be selected for the IL-3R$\alpha^{lo}$ phenotype. For selection of CMP in combination with MEP, the cells may be further selected for the phenotype CD45RA$^-$.

The progenitor cells are usually separated from other cells, e.g. hematopoietic cells, on the basis of specific markers, which are identified with affinity reagents, e.g. monoclonal antibodies. The myeloid progenitor cells lack expression of lineage specific markers. For staining purposes a cocktail of binding reagents, herein designated "lin", may be used. The lin panel will comprise binding reagents, e.g. antibodies and functional binding fragments thereof, ligands, peptidomimetics, etc., that recognize two or more of the lineage markers. A lin panel will generally include at least one marker expressed on mature B cells, on mature T cells, on mature granulocytes and on mature macrophages. Markers suitable for use in a lineage panel are typically expressed on these mature cells, but are not present on multiple lineages, or on stem and progenitor cells.

The myeloid progenitor cells are separated from a complex mixture of cells by techniques that enrich for cells having the above characteristics. For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Separation of the subject cell populations will then use affinity separation to provide a substantially pure population. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the selected cells.

The affinity reagents may be specific receptors or ligands for the cell surface molecules indicated above. In addition to antibody reagents, peptide-MHC antigen and T cell receptor pairs may be used; peptide ligands and receptor; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art. Conveniently, antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

The enriched cell population may be grown in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Specific growth factors that may be used in culturing the subject cells include steel factor (c-kit ligand), Flk-2 ligand, IL-11, IL-3, GM-CSF, erythropoietin and thrombopoietin. The specific culture conditions are chosen to achieve a particular purpose, i.e. differentiation into erythroid of megakaryocyte populations, maintenance of progenitor cell activity, etc.

Genes may be introduced into the myeloid progenitor cells for a variety of purposes, e.g. prevent HIV infection, replace genes having a loss of function mutation, provide recognition of a particular antigen, suppress activation of a particular antigen receptor, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to transfect the target cells, e.g. electroporation, calcium precipitated DNA, fusion, transfection, lipofection and the like. The particular manner in which the DNA is introduced is not critical to the practice of the invention.

Common Myeloid Progenitor (CMP).

A hematopoietic progenitor subset that can give rise to all lineages of myeloerythroid cells, but lacks the potential to differentiate into lymphoid lineages. The CMP cells may be identified and isolated by means of cell surface markers. The CMP cells of both humans and mice stain negatively for the markers Thy-1 (CD90), IL-7Rα (CD127); and with a panel of lineage markers, which lineage markers may include CD2; CD3; CD4; CD7; CD8; CD10; CD11 b; CD14; CD19; CD20; CD56; and glycophorin A (GPA) in humans and CD2; CD3; CD4; CD8; CD19; IgM; Ter110; Gr-1 in mice. The cells are CD34 positive, and CD38 positive. In humans, the CMP is also characterized as IL-3Rα$^{lo}$ CD45RA$^-$. In the mouse the CMP are Sca-1 negative, (Ly-6E and Ly-6A), c-kit high, and FcγR$^{lo}$.

The developmental potential of CMPs can be demonstrated by in vitro culture in the presence of steel factor (SLF), flt-3 ligand (FL), interleukin (IL)-3, IL-11, GM-CSF, thrombopoietin (Tpo) and erythropoietin (Epo), where the CMP cells give rise to myeloerythroid colonies including CFU-GEMMeg, burst-forming unit-erythroid (BFU-E), CFU-megakaryocytes (CFU-Meg), CFU-granulocyte/macrophage (CFU-GM), CFU-granulocyte (CFU-G) and CFU-macrophage (CFU-M).

Granulocyte/Monocyte Progenitor (GMP).

A hematopoietic progenitor subset that can give rise to monocytes and granulocyte lineages, but lacks the potential to differentiate into lymphoid, erythroid and megakaryocytic lineages. The GMP cells of both humans and mice stain negatively for the markers Thy-1 (CD90), IL-7Rα (CD127); and with a panel of lineage markers, which lineage markers may include CD2; CD3; CD4; CD7; CD8; CD10; CD11 b; CD14; CD19; CD20; CD56; and glycophorin A (GPA) in humans and CD2; CD3; CD4; CD8; CD19; IgM; Ter110; Gr-1 in mice. The cells are CD34 positive, and CD38 positive. The human cells are also IL-3Rα$^{lo}$ CD45RA$^+$, while the mouse is FcγR$^{hi}$.

The developmental potential of GMPs can be demonstrated by in vitro culture in the presence of steel factor (SLF), flt-3 ligand (FL), interleukin (IL)-3, IL-11, GM-CSF, thrombopoietin (Tpo) and erythropoietin (Epo), where the CMP cells give rise to CFU-M, CFU-G, or CFU-GM colonies containing macrophages and/or granulocytes.

Megakaryocyte/Erythroid Progenitor (MEP).

A hematopoietic progenitor subset that can give rise to megakaryocytic and erythroid cells, but lacks the potential to differentiate into lymphoid, granulocytic and monocytic lineages. The MEP cells of both humans and mice stain negatively for the markers Thy-1 (CD90), IL-7Rα (CD127); and with a panel of lineage markers, which lineage markers may include CD2; CD3; CD4; CD7; CD8; CD10; CD11b; CD14; CD19; CD20; CD56; and glycophorin A (GPA) in humans and CD2; CD3; CD4; CD8; CD19; IgM; Ter110; Gr-1 in mice. The human cells are CD34 positive, and CD38 positive, and are also IL-3Rα$^-$CD45RA$^-$, while the mouse is FcγR$^{lo}$ CD34$^-$.

Megakaryocyte Progenitor (MKP).

A hematopoietic progenitor restricted to the megakaryocytic lineage. MKP cells express detectable levels of the markers CD41, CD9 and CD34. Optionally, the cells may be further selected for a lack of expression of the markers Thy-1 (CD90), IL-7Rα (CD127); and/or with a lineage panel of markers. Other markers of interest include positive expression of CD38 and c-kit (CD117). In one embodiment of the invention, a selected set cells includes CMP, MEP and MKP cells, having the phenotype of Thy-1$^-$, IL-7Rα$^-$, lin$^-$, CD34$^+$, CD38$^+$.

As used herein, "syngeneic" refers to a cells that are genetically essentially identical with the recipient or essentially all leukocytes of the recipient. Examples of syngeneic cells include cells derived from the recipient, also referred to in the art as "autologous cells", a clone of the recipient, or an identical twin of the recipient. In animal models, congenic strains are substantially syngeneic, in that the cells are identical at all loci except for the selected congenic marker.

As used herein, "allogeneic cells" refers to a cells derived from a donor that is non-syngeneic with the recipient or non-syngeneic with a substantial proportion of the lymphocytes present in the recipient, where the donor is of the same species as the recipient or of the same species as substantially all of the lymphocytes of the recipient. Typically, non-clonal mammals of the same species are allogeneic relative to each other.

As used herein, "xenogeneic" refers to a cells of a different species than the recipient or of a different species than a substantial proportion of the lymphocytes present in the recipient.

HLA Mismatches and Typing.

Major histocompatibility complex antigens (also called human leukocyte antigens, HLA, or the H2 locus in the mouse) are protein molecules expressed on the surface of cells that confer a unique antigenic identity to these cells. MHC/HLA antigens are target molecules that are recognized by T-cells and natural killer (NK) cells as being derived from the same source of hematopoietic reconstituting stem cells as the immune effector cells ("self") or as being derived from another source of hematopoietic reconstituting cells ("non-self"). Two main classes of HLA antigens are recognised: HLA class I and HLA class II. HLA class I antigens (A, B, and C in humans) render each cell recognisable as "self," whereas HLA class II antigens (DR, DP, and DQ in humans) are involved in reactions between lymphocytes and antigen presenting cells. Both have been implicated in the rejection of transplanted organs.

An important aspect of the HLA gene system is its polymorphism. Each gene, MHC class I (A, B and C) and MHC class II (DP, DQ and DR) exists in different alleles. HLA alleles are designated by numbers and subscripts. For example, two unrelated individuals may carry class I HLA-B, genes B5, and Bw41, respectively. Allelic gene products differ in one or more amino acids in the α and/or β domain(s). Large panels of specific antibodies or nucleic acid reagents are used to type HLA haplotypes of individuals, using leukocytes that express class I and class II molecules.

The most important alleles for HLA typing are the six MHC Class I proteins expressed by the host and donor: two alleles for each of HLA-A; HLA-B and HLA-C. The myeloid progenitor cells used in the methods of the invention are typically mismatched for at least one Class I allele, and may be mismatched for two, three, four, five or all of the Class I alleles.

Any method known in the art may be optionally used to for typing the myeloid progenitor cells. For example, three main processes are currently used to perform HLA typing. The first is conventional serological cytotoxicity method, where samples of lymphocytes (taken from blood or spleen) are added to Terasaki plates. These plates hold individual wells that contain different specific antibodies (from either maternal sera or manufactured monoclonal antibodies). The best cells for class II typing are B lymphocytes, and class I typing can be performed with the remaining leucocytes. Magnetic beads are used to purify the required cells from blood or spleen. If the HLA antigen and specific antibody bind, and complement is added, the cells in that well will be killed. The pattern of wells showing this cell death allows the deduction of which combination of HLA antigens were present on the original tissue cells.

Another method used for HLA typing is flow cytometry, particularly when looking for specific alleles. Leucocytes are added to detectable labeled monoclonal antibodies specific for the HLA types of interest. The sample is then analyzed by flow cytometry to determine which antibodies have bound to the cells.

DNA typing is increasingly being used for HLA typing. This process involves extracting the DNA from cells and amplifying the genes that encode for the HLA peptides using polymerase chain reaction techniques. The genes may be matched with known HLA nucleotide sequences found stored in several gene bank databases, including the IMGT/HLA database.

Cells between individuals may also differ at minor histocompatibility antigens, or minor H antigens. Minor H antigens are peptides derived from polymorphic proteins that are presented by the MHC molecules on the graft. MHC class I molecules bind and present a selection of peptides derived from proteins made in the cell, and if polymorphisms in these proteins mean that different peptides are produced in different members of a species, these can be recognized as minor H antigens. One set of proteins that induce minor H responses is encoded on the male-specific Y chromosome. Responses induced by these proteins are known collectively as H-Y. The nature of the majority of minor H antigens, encoded by autosomal genes, is unknown, but one, HA-2, has been identified as a peptide derived from myosin.

An effective dose of one or more allogeneic myeloid progenitor cells is administered to an individual in need of enhancement of myeloid or erythroid function. An effective dose of the allogeneic myeloid progenitor cells varies within wide limits and will, of course be fitted to the individual requirements in each particular case. The number of cells used will depend on the weight and condition of the recipient and other variables known to those of skill in the art. In general, such amount is at least $10^4$ myeloid progenitor cells per kg of body weight and most generally need not be more than $3 \times 10^7$ myeloid progenitor cells/kg, usually at least about $5 \times 10^5$/kg, more usually at least about $1 \times 10^6$/kg; and not more than about $1 \times 10^7$/kg, more usually not more than about $5 \times 10^6$/kg. Where the cells are administered in combination with a cytokine, the effective dose may be reduced, for example from about $2 \times 10^5$/kg to $5 \times 10^5$/kg. The biological effectiveness of a dose may be empirically determined, e.g. in an animal model, and extrapolated for the specific patient needs and size. End points of interest include production of red blood cells sufficient to render a patient non-anemic; production of platelets sufficient to protect a patient from complications due to bleeding; production of neutrophils sufficient to protect a patient from fungal infection; and the like.

The cells can be administered by any route that is suitable for the particular tissue or organ to be treated. The cells can be administered systemically, i.e., parenterally, by intravenous injection. The cells can be suspended in an appropriate diluent, at a concentration of from about 0.5 to about $5 \times 10^6$ cells/ml. As discussed above, the cells will generally be selected first to provide a purified population comprising one or more myeloid progenitor subsets.

In a preferred embodiment, the myeloid progenitor cell preparation or composition is formulated in accordance with routine procedures as a pharmaceutical composition adapted for intravenous administration to human beings. Typically, compositions for intravenous administration are solutions in sterile isotonic aqueous buffer. Where necessary, the composition may also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also provides a pharmaceutical pack or kit comprising one or more containers filled with one or more of the ingredients of the pharmaceutical preparation of the invention. Associated with such container(s) can be a notice in the form prescribed by a governmental agency regulating the manufacture, use or sale of pharmaceuticals or biological products, which notice reflects approval by the agency of manufacture, use or sale for human administration.

The present invention is particularly advantageous in that myeloid progenitor cells may be used for a variety of treatments wherein the source of the myeloid progenitor cells is other than the recipient and without requiring that such source be matched to the recipient. Moreover, such myeloid progenitor cells may be used without requiring chronic administration of immunosuppressants.

Patients suffering from various diseases and therapies may have a deficiency on one or more myeloid lineage cells, as a result of chronic disease, infection, drug treatment, and the like. Such patients benefit from the administration of an effective dose of allogeneic myeloid progenitor cells for enhancement of myeloid and/or erythroid function. The purified cells may be formulated with biologically active agents, such as antifungal agents, antibiotics, cytokines, etc., and may comprise biological entities, such as red blood cells, platelets, hematopoietic stem cells, etc. The agents may be provided in a single formulation with the cells, or may be separately administered.

For example, patients undergoing hematopoietic cell transplantation (HCT) receive myeloablative doses of chemo-radiation therapy that lead to depletion of hematopoietic stem cells (HSC), progenitor cells and mature cells, thus leading to a phase of treatment related pancytopenia. Embodiments of interest include the treatment of such patients in conjunction with myeloablative chemotherapy or radiation therapy, where the treatment comprises co-administration of hematopoietic stem cells in combination with CMP, and one or more of the cytokines such as G-CSF and GM-CSF. Myeloid progenitors may be given as additive or synergistic therapy with antimicrobials for the treatment or prevention of infections, including antibiotics and antifungal agents.

The use of G-CSF (neupogen) in the treatment of patients after chemotherapy is known in the art, and it will be administered in doses and regimens consistent with such practice. For example, neupogen doses that accelerate neutrophil production may range from about 1 µg/kg to 100 µg/kg, and may delivered sub-cutaneously, intravenously, etc. Trials have been reported for regimens including 4-8 µg/kg SC at days 4-17; 5.75-46 µg/kg IV at days 4-17; 3.45-69 µg/kg IV at days 4-11; 23-69 µg/kg IV at days 8-28; 11.5 µg/kg IV at days 2-9; 5.75 µg/kg IV at days 10-12; and 5.45-17.25 µg/kg SC at days 6-19.

Neutropenia is a reduction in the blood neutrophil (granulocyte) count, often leading to increased susceptibility to bacterial and fungal infections. Neutropenia may be classified by the neutrophil count [(total WBC)×(% neutrophils+ bands)] and the relative risk of infection: mild (1000 to 1500/µL), moderate (500 to 1000/µL), or severe (<500/µL). Acute, severe neutropenia caused by impaired neutrophil production is often life-threatening in immunocompromised patients. Cytotoxic chemotherapy induces neutropenia because of the high proliferative rate of neutrophil precursors and the rapid turnover of blood neutrophils. Impaired neutrophil production can also occur when leukemia, myeloma, lymphoma, or metastatic solid tumors infiltrate and replace the bone marrow. Tumor-induced myelofibrosis may further extenuate neutropenia. Myelofibrosis can also occur from granulomatous infections, Gaucher's disease, and radiotherapy. Embodiments of interest include the administration of CMP, optionally in combination with GMP, where the cells are provided in conjunction with G-CSF. Patients may also benefit from the administration of antifungal agents, e.g. amphotericin, AmBisome, Abelcet, Voriconazole, Caspofungin, Itraconazole, Fluconazole; and the like.

Anemia is a lower than normal number of red blood cells (erythrocytes) in the blood, usually measured by a decrease in the amount of hemoglobin. Causes of anemia include B12 deficiency, iron deficiency, folate deficiency, hemolytic anemia, G-6-PD deficiency, idiopathic aplastic anemia, idiopathic autoimmune hemolytic anemia, immune hemolytic anemia, megaloblastic anemia, pernicious anemia, secondary aplastic anemia, sickle cell anemia, etc. Embodiments of interest for the treatment of anemia include administration of CMP and/or MEP optionally in conjunction with erythropoietin.

Erythropoietin is a glycoprotein that stimulates red blood cell production. It is produced in the kidney and stimulates the division and differentiation of committed erythroid progenitors in the bone marrow. Anemia in cancer patients may be related to the disease itself or the effect of concomitantly administered chemotherapeutic agents. The use of EPO is known in the art, and the methods of the invention are consistent with such practice. EPO has been shown to increase hematocrit and decrease transfusion requirements after the first month of therapy, in anemic cancer patients undergoing chemotherapy. Endogenous baseline serum erythropoietin levels vary among patients. In general, patients with lower baseline serum erythropoietin levels responded more vigorously than patients with higher baseline erythropoietin levels. Although no specific serum erythropoietin level can be stipulated above which patients would be unlikely to respond to therapy, treatment of patients with grossly elevated serum erythropoietin levels (e.g., >200 mUnits/mL) is not recommended. Intravenously administered EPO is eliminated at a rate consistent with first order kinetics with a circulating half-life ranging from approximately 4 to 13 hours. Within the therapeutic dose range, from about 1 to 250 U/kg, usually from about 50-150 U/kg, detectable levels of plasma erythropoietin are maintained for at least 24 hours.

Thrombocytopenia is any disorder in which there are not enough platelets. This condition is sometimes associated with abnormal bleeding. Thrombocytopenia is often divided into three major causes of low platelets: low production of platelets in the bone marrow, increased breakdown of platelets in the bloodstream, and increased breakdown of platelets in the spleen or liver. Disorders that involve low production in the bone marrow include aplastic anemia, and cancer in the bone marrow. Disorders that involve the breakdown of platelets include: immune thrombocytopenic purpura (ITP), drug-induced immune thrombocytopenia, drug-induced nonimmune thrombocytopenia, thrombotic thrombocytopenic purpura, primary thrombocythemia, disseminated intravascular coagulation (DIC), hypersplenism, etc. Embodiments of interest for the treatment of thrombocytopenia include administration of CMP, optionally combined with MEP and/or MKP. The cell function may be enhanced by co-administration of thrombopoietin.

Thrombocytopenia following myelotoxic therapy is a common problem and when severe (<20 000/μl) can lead to severe morbidity and mortality. Thrombopoietin (TPO) is a naturally occurring glycosylated peptide which stimulates the differentiation of bone marrow stem cells into megakaryocyte progenitor cells, induces the expression of megakaryocyte differentiation markers, promotes megakaryocyte proliferation, polyploidization and, ultimately, the formation of increased numbers of platelets in the circulation. TPO has now been produced by recombinant technology and has entered clinical trials. TPO will be administered according to protocols as known in the art, for example, rhTPO may be administered intravenously by bolus injection at doses ranging from 0.1 to 10 μg/kg/day every one to 3 days. G-CSF may be concomitantly administered to promote myeloid recovery. (see Bone Marrow Transplantation (2001) 27, 261-268).

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Example 1

The Ability of Allogeneic Committed Myeloid Progenitors to Protect Against Invasive Aspergillosis Following Myeloablative Treatment is not MHC-Restricted The results presented herein demonstrate that allogeneic co-transplantation of CMP/GMP protects mice against lethal invasive aspergillosis, and, of great clinical significance, this protection is not MHC restricted. The number of CMP/GMP transplanted and the MCH-antigen disparity between the host and donor did not change the functional outcome even though the quantitative reconstitution of myeloid cells was decreased in hosts with greater antigen disparity. These results further support our hypothesis that graft engineering using hematopoietic progenitor cell populations can be useful to decrease susceptibility to infections in patients undergoing HCT. Fully allogeneic myeloid progenitor transplantations could improve upon granulocyte transfusions or administration of G-CSF to overcome periods of neutropenia of any cause.

Methods

Animals.

CMP/GMP were isolated from the bone marrow of C57BL/Ka-Thy1.1.CD45.1 ($H2^b$) mice and C57BL/6.CD45.2 ($H2^b$), BALB.B ($H2^b$), or Balb/c ($H2^d$) mice were used as hosts in congenic, allogeneic MHC-matched or MHC-mismatched transplantation experiments, respectively. HSC were isolated from the bone marrow of C57BL/Ka-Thy1.1.CD45.2 ($H2^b$) or B10.D2.Thy1.1 ($H2^d$) mice. The use of these mouse strain combinations allowed differentiation between the CMP/GMP-derived cells and the host or HSC-derived cells. All mice were bred and maintained at the animal care facility at Stanford University School of Medicine. Donor mice were used at 6-8 weeks and hosts at 8-14 weeks of age.

Cell Sorting and Flow Cytometric Analysis.

To isolate c-Kit$^+$Thy1.1$^{lo}$Lin$^-$Sca-1$^+$ HSC, whole bone marrow cells (WBMC) from femurs and tibiae were depleted of mature erythrocytes via ammonium chloride lysis and then stained with biotinylated rat anti-mouse c-Kit (3C11) followed by streptavidin immunomagnetic beads (Miltenyi Biotec, Auburn, Calif.) as described previously. c-Kit$^+$ cells were positively selected using an autoMACS cell separator (Miltenyi Biotec, Auburn, Calif.). Cells enriched for HSC were stained with PE-conjugated anti-CD3 (145-2C11, Pharmingen, San Diego, Calif.), anti-CD4 (GK1.5), anti-CD5 (53-7.8), anti-CD8 (53-6.7), anti-B220 (6B2), anti-Ter119, anti-Mac-1 (M1/70), and anti-Gr-1 (RB6-8C5) and FITC-conjugated anti-Thy1.1 (19XE5), Texas Red (TxR)-conjugated anti-Sca-1 (E13-161) and allophycocyanin (APC)-conjugated anti-c-Kit (2B8).

To isolate Lin$^-$Sca-1$^-$c-Kit$^+$CD34$^+$FcγR$^{lo}$ CMP and Lin$^-$Sca-1$^-$c-Kit$^+$CD34$^+$FcγR$^{hi}$ GMP, WBMC from C57BL/Ka-Thy1.1.CD45.1 mice were depleted of mature erythrocytes via ammonium chloride lysis and then stained with biotinylated rat antibodies against the lineage (Lin) markers IL-7Rα-chain (A7R34), CD19 (1D3, Pharmingen, San Diego, Calif.), immunoglobulin M (IgM, Pharmingen, San Diego, Calif.), Thy1.1 (19XE5), and unconjugated rat antibodies against Ter119, Gr-1 (RB6-8C5), and Cy5-PE conjugated rat anti-mouse CD45R/B220 (RA3-6B2, Pharmingen, San Diego, Calif.). The Lin$^+$ cells were partially removed following incubation with sheep anti-rat Dynabeads (Dynal, Oslo, Norway) and magnetic depletion. Cells enriched for progenitors were then stained with CD45R/B220 (RA3-6B2, Pharmingen, San Diego, Calif.), streptavidin Cy5-PE and goat anti-rat Cy5-PE (RED670, Gibco, Gaithersburg, Md.), TxR-conjugated anti-Sca-1 (E13-161), APC-conjugated anti-c-Kit (2B8), FITC-conjugated anti- CD34 (RAM34, Pharmingen, San Diego, Calif.), and PE-conjugated anti-CD16/32 (2.4G2, Pharmingen, San Diego, Calif.).

The reconstitution analysis of cellular subpopulations in blood, spleen and bone marrow samples was accomplished by depleting mature erythrocytes via ammonium chloride lysis and then staining with antibodies in various combinations including TxR or APC-conjugated anti-CD45.1 (A20.1.7), TxR-conjugated anti-Mac-1 (M1/70), PE-conjugated anti-Gr-1, FITC-conjugated anti-Ter119, PE-conjugated anti-MHC class II (I-A/I-E, M5/114.15.2, Pharmingen, San Diego, Calif.), APC-conjugated anti-CD11c (HL3, Pharmingen, San Diego, Calif.). Antibody staining and washing was performed using HBSS with penicillin/streptomycin (Gibco BRL, Grand Island, N.Y.) and 2% heat-inactivated fetal bovine serum FBS (SIGMA, St. Louis, Mo.). Cells were incubated 20-30 minutes at 4° C., and washed twice. Dead cells were excluded by propidium iodide staining.

Cell sorting and analysis were performed on a modified dual laser fluorescence-activated cell sorter (FACSVantage, BD Biosciences, San Jose, Calif.) equipped with a 488-nm argon and a 595-nm dye laser made available through the FACS shared user group at Stanford University.

Irradiation and Transplantation.

C57BL/6 hosts were irradiated with 9.5 Gy, BALB.B or Balb/c hosts with 8 Gy, in 2 fractions, 3-4 hours apart, using a 200-kV x-ray machine (Philips RT250, Shelton, Conn.) and given antibiotic water (1.1 g/L neomycin sulfate and $10^6$ U/L polymyxin B sulfate) after irradiation. Mice were anesthetized with Isoflurane (Abbott Laboratories, Abbott Park, Ill.) and cells were injected into the retro-orbital venous plexus using 0.5 cc insulin syringes with 28 Ga needles (Applied Scientific, South San Francisco, Calif.).

Cell Counts.

Blood samples were submitted to the diagnostic laboratory of the Department of Comparative Medicine at Stanford University where complete blood counts (CBC) including differential counts were performed on a Cell DYN 3500 (Abbott Laboratories, Abbott Park, Ill.). Single cell suspensions of splenocytes were stained with Turks solution and counted manually using a hemocytometer.

*Aspergillus fumigatus* Infection.

A clinical isolate of *Aspergillus fumigatus* that had caused fatal sinusitis in a patient following allogeneic HCT was used in these experiments and prepared as described previously. On day 7 post-transplantation, mice were infected intravenously (i.v.) via lateral tail vein with 100 conidia *Aspergillus fumigatus* in a total volume of 150 µl sterile normal saline. The infections were performed by a single individual who was blinded to the experimental groups. Mice were weighed daily and examined twice daily following infection.

Statistical Analysis.

For comparison of absolute cell counts, the rank sum test was performed. We used the log-rank test to compare groups in Kaplan Meier survival analysis.

Results

Rapid Myeloid Reconstitution from Allogeneic CMP/GMP.

In order to determine if MHC-antigen disparity influenced engraftment of myeloid progenitors, CMP/GMP-derived cells were quantitated in blood, spleen, and bone marrow on day 7 post-transplantation. Myeloid progenitor engraftment after transplantation from congenic, MHC-matched or MHC-mismatched donors was compared. Donor-host mouse strain pairings are shown in Table 1.

TABLE 1

| Experiment type | CMP/GMP donor | HSC donor | Host | CMP/GMP Antigen Disparity |
|---|---|---|---|---|
| Function | C57BL/6-Ly5.2 | C57BL/Ka-Thy1-1 | BALB.B | MHC-matched unrelated |
| Function | C57BL/6-Ly5.2 | B10.D2.Thy1.1 | Balb/c | MHC-mismatched |
| Quantitative engraftment | C57BL/6-Ly5.2 | none | C57BL/6 | congenic |
| Quantitative engraftment | C57BL/6-Ly5.2 | none | BALB.B | MHC-matched unrelated |
| Quantitative engraftment | C57BL/6-Ly5.2 | none | Balb/c | MHC-mismatched |

At this time-point, analysis of peripheral blood of mice in all groups (Table 1, groups 1 to 3) confirmed a significant peripheral blood neutropenia with low white blood cell and low absolute neutrophil counts that were not statistically significant between the three groups although a tendency to lower counts with increasing antigen disparity was observed (Table 2). Reliable FACS analysis from peripheral blood to determine CMP/GMP-derived chimerism could not be performed because of the low number of white blood cells within the samples. Red blood cell counts were within the normal range and were not different between the groups.

TABLE 2

| | Reconstitution from CMP/GMP | | | | | |
|---|---|---|---|---|---|---|
| | congenic | | matched unrelated | | MHC-mismatched | |
| cell type | unit | mean | SD | mean | SD | mean | SD |
| Blood | | | | | | | |
| RBC | $\times 10^6/\mu l$ | 7 | 3 | 9 | 0 | 8 | 1 |
| Hematocrit | % | 31 | 12 | 40 | 2 | 39 | 3 |

TABLE 2-continued

Reconstitution from CMP/GMP

| cell type | unit | congenic mean | congenic SD | matched unrelated mean | matched unrelated SD | MHC-mismatched mean | MHC-mismatched SD |
|---|---|---|---|---|---|---|---|
| WBC | /μl | 200 | 310 | 91 | 79 | 78 | 88 |
| ANC | /μl | 125 | 183 | 60 | 47 | 38 | 34 |
| Spleen | | | | | | | |
| total CMP/GMP derived | ×10$^5$ | 43.9 | 14.0 | 21.8 | 13.1 | 1.4 | 1.7 |
| Total granulocytes | | 26.6 | 9.3 | 10.5 | 6.5 | 0.8 | 1.1 |
| CMP/GMP-derived granulocytes | | 26.6 | 9.3 | 10.5 | 6.5 | 0.8 | 1.1 |
| Bone Marrow | % | | | | | | |
| % CMP/GMP-derived | | 42.9 | 16.8 | 35.3 | 16.1 | 20.1 | 10.8 |
| % granulocytes | | 50.4 | 13.5 | 59 | 11.7 | 71.8 | 5.8 |
| % granulocytes CMP/GMP derived | | 77.4 | 8.8 | 81.3 | 5.1 | 83.6 | 5.1 |

In contrast, high CMP/GMP-derived chimerism was detected in spleen and bone marrow (Table 2). In spleen and bone marrow, the majority of CMP/GMP-derived cells were mature granulocytes as defined by the co-expression of the two markers Mac-1 and Gr-1. The remaining cells were either erythroid cells (Ter119$^+$) or cells of the dendritic cell lineage (CD11c$^+$MHC II$^+$). With increasing degrees of antigen disparity between donor and host, the engraftment efficiency of the CMP/GMP populations decreased. When compared to congenic donor-host pairs, transplantation of allogeneic MHC-matched CMP/GMP was not significantly different in absolute or relative number of CMP/GMP-derived cells. There was no significant difference in the percentage of CMP/GMP-derived cells in the bone marrow of either allogeneic group when compared to congenic donor-host pairings (FIG. 1C and Table 2).

CMP/GMP did not give rise to cells of the lymphoid lineage and their myeloid progeny could not be detected in blood, spleen or bone marrow later than day 28 post-transplantation, confirming the purity of the sorted cell populations.

Co-Transplantation of Allogeneic CMP/GMP Protects Against Lethal *Aspergillus fumigatus* Infection.

Figure 2A:
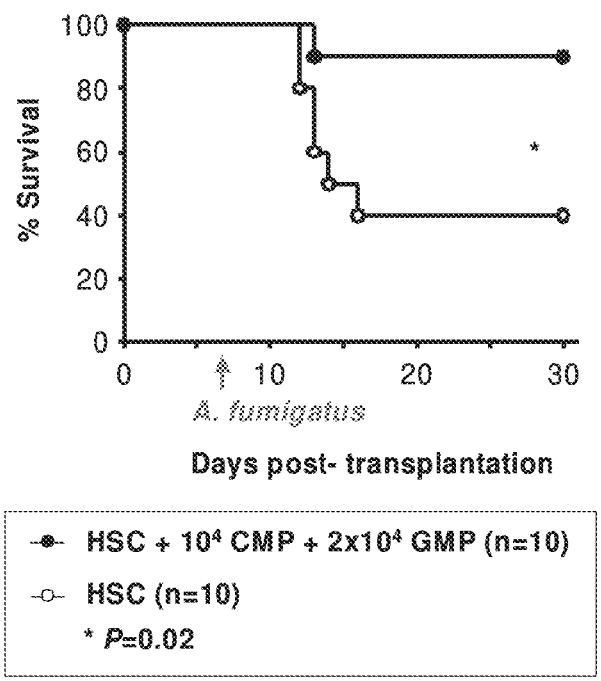
Figure 3A:
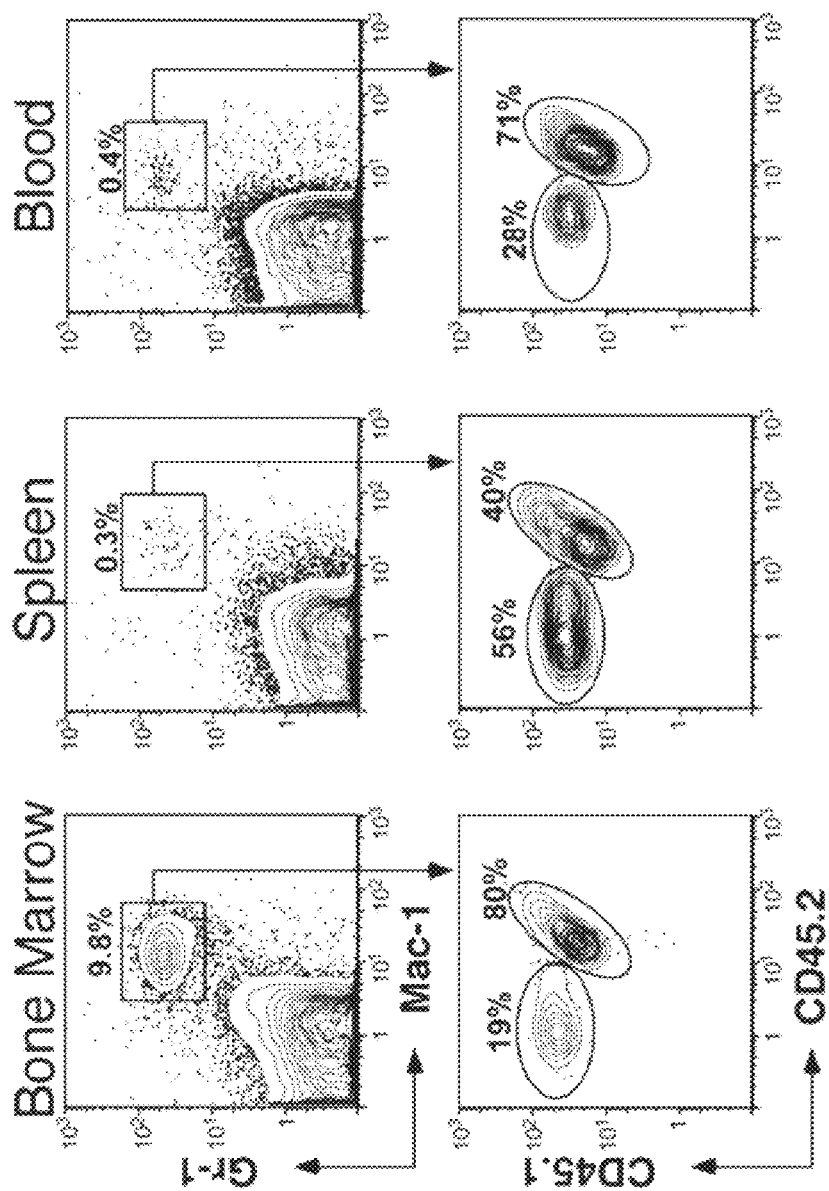
FIG. 3A-3B. Analysis of the tissue distribution of CMP/GMP progeny and survival following *A. fumigatus* infection. (A) Flow cytometric analysis of tissue neutrophils (Mac-$1^+$Gr-$1^+$) on D+8 identified the presence of donor CMP/GMP-derived cells (CD45.$1^+$CD45.$2^-$). Although present in both bone marrow and blood, the donor cells constituted the majority of splenic neutrophils in comparison to host cells (CD45.$1^+$CD45.$2^+$). (B) Kaplan-Meier plot of mice infected with 3-4×$10^6$ cfu of *A. fumigatus* following treatment with 5-FU only (open circles) or 5-FU+1×$10^3$ CMP and 2×$10^3$ GMP (closed circles). The myeloid progenitors were infused 30 hours after 5-FU administration and the mice were infected 8 days post-chemotherapy via intranasal instillation of *A. fumigatus* conidia. The group that had received the CMP/GMP infusion (n=41) had a significantly higher survival rate than the group treated with 5-FU only (n=75) (56% and 33% respectively; P=0.019). Animals that succumbed to infection at 2-4 days post-instillation showed clinical evidence of disease, whereas those that survived appeared healthy throughout the observation period (30-60 days).
Figure 3B:
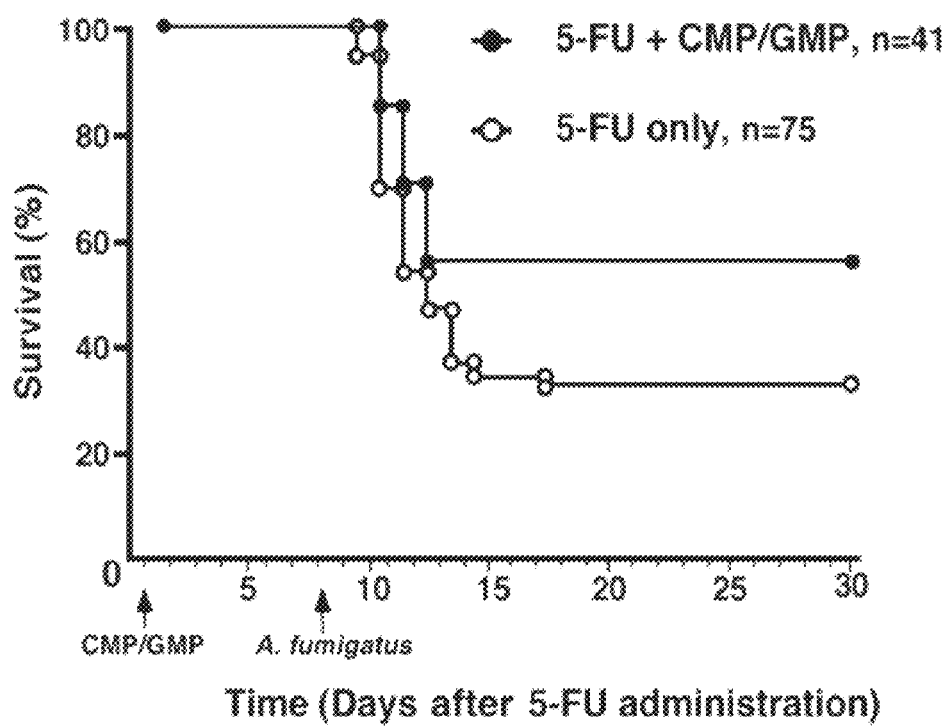

In a separate series of experiments, designed to study the function of MHC-matched allogeneic CMP/GMP, lethally irradiated mice were co-transplanted with 10$^4$ CMP, 2×10$^4$ GMP and 500 HSC (Table 1 group 4). Mice that received grafts containing 500 HSC alone were used as controls. On day 7 post-transplantation, all mice were infected with 100 conidia of *A. fumigatus* intravenously. Mice that received grafts containing CMP/GMP were protected against lethal fungal challenge when compared to mice that received grafts containing HSC alone (P=0.02, FIG. 2A).

In order to determine if functional engraftment of myeloid progenitors was MHC-restricted, MHC-mismatched allogeneic mice were used as CMP/GMP donors. Using the same study design as was used for MHC-matched donor-host pairings, groups of lethally irradiated mice received grafts containing the same number of CMP/GMP and HSC (Table 1 group 5). Mice that received grafts containing CMP/GMP from MHC-mismatched donors were protected against lethal invasive aspergillosis as compared to mice transplanted with HSC alone. Furthermore, increasing the dose of transplanted CMP/GMP fourfold did not significantly improve survival (P<0.0001, FIG. 2B). Regardless of the differences in engraftment pattern described above, protection against invasive aspergillosis was comparable between all groups.

In the study presented here, we demonstrate that co-transplantation of allogeneic CMP/GMP functionally improves immune reconstitution following HSC transplantation. Inclusion of CMP/GMP in the graft accelerates reconstitution of the tissue myeloid pool that protects mice against invasive aspergillosis early post-transplant. Of greatest clinical importance regarding the utility of such cellular therapy is the observation that this protection is not MHC-restricted.

Patients undergoing HCT are at high risk for developing invasive fungal infections—especially due to molds such as *Aspergillus fumigatus*—which are associated with a high morbidity and mortality despite the development of new antifungal agents and supportive strategies such as granulocyte transfusions or use of hematopoietic growth factors. Furthermore, establishing the diagnosis is often difficult involving clinical, radiological, microbiological and histopathological examinations. Therefore, strategies to reduce susceptibility to infection are crucial for the outcome. Furthermore, it is of great importance to develop new therapeutic approaches to prevent the establishment of bacterial or invasive fungal infections which would not be dependent on antimicrobial therapy and the attendant risks of inducing resistance. Although the risk factors for invasive aspergillosis post-transplantation are not restricted to neutropenia, the biology and normal immune defenses against this mold make it a prototypic pathogen to determine whether or not functional myeloid reconstitution has been achieved.

The immune response to *Aspergillus fumigatus* involves cells of the innate (macrophages and neutrophils, first lines of defense) and cells of the adaptive immune system as second lines of defense (dendritic cells and T cells). CMP/GMP are progenitors committed to myeloid lineage development, have lost the self-renewal capacity and give rise to all cells of the myeloid lineage including granulocytes, monocytes, megakaryocytes, erythrocytes and dendritic cells. We previously reported that inclusion of CMP/GMP to the graft of pure HSC could accelerate and functionally improve the reconstitution of myeloid effector cells in the setting of congenic donor-host pairings. We now demonstrate that allogeneic CMP/GMP are similarly effective and function in a non-MHC-restricted fashion.

In our experiments, CMP/GMP engraftment was detected in the bone marrow and spleen as early as 4 days post-transplantation and was robust by day 7 post-transplantation in all three donor-host strain combinations tested. Other studies assessing in vivo trafficking of purified HSC and multipotent hematopoietic progenitor cell populations revealed bone marrow as well as spleen to be the primary homing and proliferation sites of early hematopoietic cell populations following myeloablative treatment. Although we did not perform real time imaging studies in living animals, our results suggest that CMP/GMP rapidly home to their biological niches (bone marrow and spleen) and start proliferation similar to other early hematopoietic progenitor cell populations. Furthermore, these events seem to occur regardless of MHC disparity, albeit less frequently in MHC mismatched hosts.

The barrier to HSC engraftment associated with increasing degrees of MHC-mismatch consists of host T and NK cells and has been well documented in mice, however the underlying mechanisms for these observations remain to be elucidated. HSC did not appear to be directly targeted by NK cells. In order to achieve the same HSC function—measured as radioprotection—10-60 fold higher numbers of purified HSC needed to be transplanted into an MHC-mismatched mouse as compared to a congenic mouse. Therefore, we expected that transplantation of CMP/GMP into allogeneic recipients would result in reduced engraftment when compared to congenic transplantation. In our experiments, reconstitution from CMP/GMP was quantitatively reduced with increasing degrees of antigen disparities. Qualitatively, CMP/GMP gave rise to all cells of the myeloid lineage with the same profile of distribution as in congenic hosts. Interestingly, peripheral blood neutropenia was present in all donor-host pairings tested, suggesting that CMP/GMP reconstitute the tissue myeloid pool before peripheral blood neutropenia is resolved.

Although transplantation of CMP/GMP from MHC-mismatched donors resulted in quantitatively fewer progenitor-derived cells in the spleen and bone marrow, protection against invasive aspergillosis in MHC-matched and MHC-mismatched donor-host pairings was preserved. Thus, protection was not MHC-restricted indicating that CMP/GMP co-transplantation mainly acts on improving the innate arm of immunity against *A. fumigatus*. This is consistent with results from our previous study where in vivo depletion of granulocytes using anti-Gr-1 antibody abrogated the protective effect of CMP/GMP co-transplantation. Interestingly, increasing the number of transplanted CMP/GMP by 4-fold did not result in better protection. As demonstrated in the setting of congenic transplantation, a relatively modest augmentation of the myeloid tissue pool was sufficient to protect mice against invasive aspergillosis and peripheral blood neutropenia did not correlate with effective antifungal immune response.

In conclusion, these data show that the inclusion of CMP/GMP in the graft protects mice against lethal invasive aspergillosis in the early phase post-transplantation. Although the engraftment is quantitatively less in MHC-mismatched recipients, the function measured as protection against invasive aspergillosis is conserved. These data demonstrate that the human counterpart of these progenitors, analogous to the infusion of other blood products, can be collected from unrelated donors. This can provide feasible therapy with a broader range of applicability as adjunctive treatment to decrease susceptibility to fungal infections resulting from neutrophil dysfunction or depletion.

Example 2

Single Infusion of Myeloid Progenitors Reduces Death from *Aspergillus fumigatus* Following Chemotherapy-Induced Neutropenia Hematopoietic progenitors committed to the myeloid lineage, the common myeloid and granulocyte-monocyte progenitors (CMP/GMP) have been shown to protect against opportunistic pathogens following myeloablative radiation; however, the efficacy of this approach has not been studied in the setting of chemotherapy-induced neutropenia. In this mouse model, the infusion of CMP/GMP on the day after 5-fluorouracil (5-FU) administration (D+1) resulted in a significant increase in the number of splenic neutrophils by D+8 when compared to 5-FU only controls (P=0.02), the majority of which were CMP/GMP-derived (54%). Moreover, 19% and 28% of neutrophils in the blood and bone marrow, respectively, were CMP/GMP-derived. Survival following intranasal challenge with the fungus *Aspergillus fumigatus* was significantly higher in CMP/GMP-infused mice than the controls (56% and 33% respectively; P=0.019). Thus, a single infusion of CMP/GMP enhances tissue neutrophil content and increases survival against a lethal challenge with *A. fumigatus* in the setting of chemotherapy-induced neutropenia.

Materials and Methods

Mice.

The F1 generation of the congenic strains of C57BL/Ka-Thy1.1 (CD45.2) and C57BL/Ka-Thy1.1 (CD45.1) mice was used as host mice. Donor myeloid cell progenitors were purified from the C57BL/Ka-Thy1.2 (CD45.1) strain. All mice were bred and maintained at the animal care facility at Stanford University School of Medicine. Donor mice were used at 6-8 weeks and recipients at 12-16 weeks.

5-FU Treatment.

A single dose of 150 mg/kg of 5-FU (American Pharmaceutical Partners Inc.; Schaumburg, Ill.) was administered intravenously 30 hours prior to myeloid progenitor cell transplantation.

Myeloid Progenitor Cell Isolation and Transplantation.

Myeloid progenitor cells were purified from whole bone marrow as described previously. Briefly, CMP and GMP were identified and isolated by (1) excluding cells expressing: IL-7Rα-chain, CD19, IgM, Thy 1.1, Ter119, Gr-1, and CD45R/B220; and (2) the positive CMP/GMP markers, c-kit, Sca-1, CD34, and CD16/32. Cells were sorted using a modified fluorescence-activated cell sorter (FACSVantage, BD Biosciences; San Jose, Calif.). Host mice were anesthetized (Isoflurane; Abbott Laboratories; N. Chicago, Ill.) and cells were transplanted into the retro-orbital cavity. Mice were observed until fully recovered.

Preparation of *A. fumigatus* Conidia.

A clinical isolate of *A. fumigatus* that had caused fatal sinusitis in a patient following allogeneic bone marrow transplantation was used to generate a conidial suspension as described previously. Suspensions were maintained at 4° C.

The *A. fumigatus* conidia stock was diluted with sterile saline to a concentration of $3-4 \times 10^6$ cfu/20-30 µl. Mice were anesthetized with Avertin administered intraperitoneally (375 mg/kg). *A. fumigatus* conidia were instilled intranasally with a precision microliter pipette (Rainin; Emeryville, Calif.).

Mice were killed when exhibiting clinical evidence of disease or on the specified study days. Lungs were harvested for histologic examination and/or cultured onto Sabouraud dextrose agar plates (BD Biosciences; Cockeysville, Md.) for fungal colonies.

Statistics.

The log-rank test was performed on the survival results and the rank sum test was used to assess the significance of the absolute leukocyte counts.

Results and Discussion

To assess the duration of the neutropenia resulting from the administration of 5-FU, peripheral blood leukocyte counts were measured at weekly intervals. Eight days (D+8) following the administration of 5-FU, the absolute leukocyte counts in both experimental groups (5-FU only vs. 5-FU+CMP/GMP) was only slightly lower than the lower limit of normal; however, mice in both groups demonstrated profound neutropenia (Table 3). By D+13, total leukocyte and absolute neutrophil counts had rebounded to above normal levels in both groups. In order to determine the early trafficking of CMP and GMP progeny, immunophenotypic analyses of peripheral blood, spleen, and bone marrow cells was performed on D+8. By this time, mice that had received a single infusion of $1 \times 10^4$ CMP and $2 \times 10^4$ GMP had a significantly higher number of splenic Mac-$1^+$Gr-$1^+$ neutrophils than the 5-FU only group (Table 3, P=0.02). Moreover, 54% of these splenic Mac-$1^+$Gr-$1^+$ neutrophils were derived from the donor CMP/GMP population. Therefore, the contribution of the myeloid progenitor populations more than doubled the total neutrophil pool in the spleen compartment. Moreover, CMP/GMP-derived Mac-$1^+$Gr-$1^+$ neutrophils were also identified in blood and bone marrow (FIG. 4A). These data demonstrate that CMP and GMP migrate and home to hematopoietic sites thus suggesting a functional engraftment in this model of chemotherapy-induced neutropenia.

TABLE 3

Absolute leukocyte counts following 5-FU treatment +/− myeloid progenitor infusion

|  | 5-FU only | | 5-FU + CMP/GMP | |
| --- | --- | --- | --- | --- |
|  | D + 8 | D + 13 | D + 8 | D + 13 |
| BLOOD | n = 15 | n = 7 | n = 9 | n = 5 |
| Absolute WBC counts ($\times 10^3$/µl) (ref. range: 5.5-9.3) | 4.1 ± 0.4 | 12.0 ± 1.6 | 5.4 ± 0.5 | 13.0 ± 0.6 |
| Absolute Neutrophil counts ($\times 10^3$/µl) (ref. range: 0.825-2.604) | 0.002 ± 0.007 | 3.6 ± 0.8 | 0.03 ± 0.01 | 2.6 ± 0. |
| SPLEEN | n = 14 | | n = 10 | |
| Absolute splenocytes ($\times 10^8$) | 3.3 ± 0.4 | ND | 4.5 ± 1.1 | ND |
| Total Mac-$1^+$Gr-$1^+$ ($\times 10^6$) | 0.6 ± 0.2 | ND | 1.2 ± 0.3* | ND |
| CMP/GMP-derived ($\times 10^5$) |  |  | 6.5 ± 2.0 (54)[†] | ND |

Data is mean absolute cell counts ± SEM.
*significant difference from D + 8 counts (P = 0.02).
ND, not determined.
[†]indicates percentage of total Mac-$1^+$Gr-$1^+$ cells.

As potentially important immune effectors, tissue was analyzed for their content of dendritic cells, macrophages, and monocytes. Although host-derived myeloid DCs (CD11c+Mac-1+) and plasmacytoid DCs (CD11c+B220+) were identified in the bone marrow and spleen, there were no CMP/GMP-derived DCs in these tissues. There was no significant difference in the total DCs between the two experimental groups in bone marrow and spleen of both the myeloid and plasmacytoid DCs (p=0.28 vs. p=0.86 and p=0.26 vs. p=0.89, respectively). Moreover, neither host-derived nor progenitor-derived DCs were identified in the peripheral blood. Similarly, no CMP/GMP-derived monocytes/macrophages (Mac-$1^+$Gr-$1^-$) were identified in any compartment and analysis of absolute splenic counts of host-derived Mac-$1^+$Gr-$1^-$ cells confirmed that there was no significant difference between the two experimental groups of 5-FU only vs. 5-FU+CMP/GMP (p=0.16).

The significance of these quantitative differences in Mac 1+Gr1+ cells was confirmed by the ability of the infusion of CMP and GMP to protect against lethal challenge with *A. fumigatus*. Following intranasal instillation of $3-4 \times 10^6$ conidia, only 33% of the animals that had received only 5-FU survived (n=75) compared with 56% of the group infused with CMP/GMP (n=41, P=0.019)(FIG. 4B). The majority of mice died within 3 days post-infection. Cultures of organs confirmed the presence of the *A. fumigatus* in the lungs. The absence of *A. fumigatus* in other tissues may be explained by the rapid morbidity and mortality due to the infection. Of note, the CMP/GMP infusions were well tolerated and histological evaluations did not reveal evidence of pulmonary injury attributable to the infusion of cells such as a diffuse neutrophilic infiltration. A neutrophilic infiltrate proximately associated with the presence of hyphae was observed in the lung tissue of about half of the mice that had received the single infusion of progenitors; in contrast, this infiltrate was not observed in the mice that had received 5-FU alone.

These data confirm that a single infusion of myeloid progenitor cells reduces susceptibility to infection with *A. fumigatus* in a preclinical model of chemotherapy-induced neutropenia. Moreover, the infusion of CMP/GMP resulted in the ability to contain a rapidly invasive infection when introduced in the biologically relevant route of inhalation. We previously reported that following transplantation, the tissue and not the peripheral blood content of myeloid effectors correlates with effective innate immunity and the in vivo depletion of Mac-$1^+$Gr-$1^+$ cells abrogated this protection. Thus, it is reasonable to conclude that the containment of infection results from appropriate homing to the site of infection.

In contrast to the efficacy of the single infusion of GMP/GMP, the use of mature granulocytes in clinical settings require repeated infusions of freshly apheresed cells which is not only cumbersome but likely engenders the production of anti-leukocyte antibodies. Additionally, in studies where the cells were characterized, up to 20% of the apheresed cells were not granulocytes and may have contributed to the beneficial or detrimental effects observed. As was observed following myeloablative radiation, CMP/GMP infusion was well tolerated even in these mice with a less severe degree of immunosuppression. It is interesting to note that the use of G-CSF to mobilize leukocytes may result in a more rapid and durable elevation of the peripheral blood leukocyte counts when compared to counts following infusions of dexamethasone-mobilized cells. Whether or not G-CSF administration influences the mobilization, proliferation, or function of the infused cells remains an area of investigation. G-CSF administration following transplantation of CMP/GMP shortened the period of susceptibility to lethal fungal infection following myeloablative radiation.

As human myeloid progenitors have already been characterized in the bone marrow and G-CSF-mobilized peripheral blood, these data support further investigation into the feasibility of cellular based therapies to replenish depleted cell populations or serve as a bridge pending recovery of the hematopoietic system following chemotherapy or radiation. The methods also provide a means of ameliorating anemia and bleeding in patients suffering from a red blood cell and/or thrombocytic deficiency.

Example 3

Role of Myeloid Progenitors in Protection Against Radiation-Induced Gut Injury

Gastrointestinal mucositis is a serious complication of intensive chemotherapy and radiotherapy (XRT), resulting in severe pain, impaired nutrition, and an increased susceptibility to infection. As shown above, a single infusion of common myeloid and granulocyte-monocyte progenitors (CMP/GMP, c-kit+Sca1+CD34 CD16/32+Lin-Thy1-) protected mice against lethal challenge with bacterial or fungal pathogens following chemotherapy or myeloablative radiation. Additionally, this protection is not HLA-restricted and correlated with the tissue myeloid content.

CMP/GMP infusion against radiation-induced injury in the gastrointestinal mucosa and liver is now shown. Following 950 cGy irradiation, Balb/c mice received infusions of one of the following: [1] hematopoietic stem cells (HSC, c-kit+Thy1loLin-Sca-1+); or [2] freshly isolated 10,000 CMP/20,000 GMP+HSC. In all cases, the HSC were MHC-matched (H2d), and CMP/GMP were MHC mismatched (H2b). A cohort of mice served as XRT controls. Mice were sacrificed at d+6 or d+9 post-transplantation.

Gross examination of the gastrointestinal tissue showed that mice in the XRT and HSC groups had severe hemorrhagic diarrhea in contrast to the mild to moderate diarrhea observed in the group receiving freshly isolated CMP/GMP or the expanded CMP/GMP. At both time points, histologic examination of gastrointestinal tissue from the XRT controls revealed sub-mucosal bleeding in gastric and intestinal tissue; necrosis and ulceration in the stomach; crowding of epithelial cells near the villi in the small intestine; and ulcerative areas and small foci of inflammation in the colon; and necrosis, portal tract damage, and dilated sinusoids/central veins in the liver.

In comparison, the histologic changes were significantly less dramatic in the stomachs, colons, and livers of the mice that had received either freshly isolated or in vitro expanded CMP/GMP. In a parallel experiment, irradiated mice were transplanted with CMP/GMP from transgenic FVB.luc+ mice that constitutively express firefly luciferase. Imaging of the living mice and harvested organs at d+6 and d+9 post-transplantation indicated the presence of CMP/GMP in the stomach and intestinal tissue, correlating with sites of attenuated XRT damage in our histologic analysis.

These findings support the clinical observation that repletion of the myeloid progenitor pool plays an important role in enhancing the recovery of radiation-injured mucosa.

All publications mentioned herein are incorporated herein by reference for the purpose of describing and disclosing, for example, the compounds and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. A method of providing myeloid function to a human patient in need thereof, said method comprising:
transplanting into said human patient a biologically effective dose of allogeneic human myeloid progenitor cells.

2. The method according to claim 1, wherein said myeloid progenitor cells comprise at least one Class I HLA mismatch relative to said individual.

3. The method according to claim 1, wherein said allogeneic myeloid progenitor cells are common myeloid progenitor (CMP) cells.

4. The method according to claim 1, wherein said allogeneic myeloid progenitor cells further comprise granulocyte/monocyte progenitors (GMP).

5. The method according to claim 1, further comprising the administration of G-CSF to said human patient.

6. The method according to claim 1, further comprising the step of administering GM-CSF to said individual.

7. The method according to claim 1, further comprising the administration of an anti-fungal or antibacterial agent to said individual.

8. The method according to claim 1, wherein said allogeneic myeloid progenitor cells further comprise myeloid erythroid progenitors (MEP).

9. The method according to claim 8, further comprising the step of: administering erythropoietin to said individual.

10. The method according to claim 1, wherein said allogeneic myeloid progenitor cells further comprise megakaryocyte progenitors (MKP).

11. The method according to claim 10, further comprising the step of: administering thrombopoietin to said individual.

12. The method according to claim 1,
wherein said cells are enriched prior to said transplanting step by the method of combining reagents that specifically recognize Thy-1, IL-7Rα (CD127), and a lineage panel with a sample of hematopoietic cells; and selecting for those cells that are Thy-1$^-$, IL-7Rα (CD127)$^-$, and lineage panel$^-$, to provide an enriched population of cells having myeloid progenitor activity.

13. The method according to claim 12, wherein said lineage panel includes CD2; CD3; CD4; CD7; CD8; CD10; CD11 b; CD14; CD19; CD20; CD56; and glycophorin A (GPA).

14. The method according to claim 12, wherein said sample of hematopoietic cells is bone marrow.

15. The method according to claim 12, wherein said sample of hematopoietic cells is mobilized peripheral blood.

16. The method of claim 3, wherein said common myeloid progenitors are enriched by combining reagents that specifically recognize IL-3Rα, and CD45RA; and selecting for those cells that are IL-3Rα$^{lo}$ CD45RA$^-$.

17. The method according to claim 8, wherein said erythroid/megakaryocyte committed progenitor cells are enriched by combining reagents that specifically recognize IL-3Rα, and CD45RA; and selecting for those cells that are IL-3Rα$^-$ CD45RA$^-$.

18. The method of claim 1 wherein the individual is immunocompromised.

19. The method of claim 1 wherein the individual is suffers from neutropenia.

20. The method of claim 1 wherein the biologically effective dose of allogeneic human myeloid progenitor cells comprises at least about 75% allogeneic myeloid progenitor cells.

21. The method of claim 1 wherein, wherein said myeloid progenitor cells comprise at least two Class I HLA mismatch relative to said individual.

22. The method of claim 1 wherein said myeloid progenitor cells comprise at least three Class I HLA mismatch relative to said individual.

23. The method of claim 1 wherein the biologically effective dose is at least $10^4$ myeloid progenitor cells/kg body weight.

24. The method of claim 1 wherein the biologically effective dose is at least about $5 \times 10^5$ myeloid progenitor cells/kg body weight.

25. The method of claim 1 wherein the biologically effective dose is at least about $1 \times 10^6$ myeloid progenitor cells/kg body weight.

26. The method of claim 1 wherein the cells are administered parenterally.

27. The method of claim 1 wherein the cells are administered intravenously.

28. The method of claim 1 further comprising transplanting into said individual hematopoietic stem cells.

* * * * *